United States Patent [19]
Sharma

[11] 4,319,882
[45] Mar. 16, 1982

[54] METHOD FOR DETECTING IMMUNOLOGICAL AGGLUTINATION AND BIOCHEMICAL AGENT THEREFOR

[76] Inventor: Yash Sharma, 2766 January Cts., Falls Church, Va. 22043

[21] Appl. No.: 123,432

[22] Filed: Feb. 21, 1980

[51] Int. Cl.$^3$ .................... G01N 33/54; G01N 33/80
[52] U.S. Cl. ................................. 23/230 B; 23/915; 252/174.22; 252/551; 422/73; 424/11; 424/12
[58] Field of Search .................. 23/230 B; 424/11, 12; 252/174.22, 551

[56] References Cited

U.S. PATENT DOCUMENTS

| | | | |
|---|---|---|---|
| 3,334,018 | 8/1967 | Smythe | 23/230 B |
| 3,432,268 | 3/1969 | Unger | 23/230 B |
| 3,624,223 | 11/1971 | Smythe | 23/230 B X |
| 4,000,121 | 12/1976 | Garcia | 424/11 X |
| 4,104,031 | 8/1978 | Robuchon-Merovak | 424/11 X |
| 4,130,395 | 12/1978 | Chryssanthou | 424/11 X |
| 4,148,869 | 4/1979 | Deaton | 424/11 |
| 4,184,848 | 1/1980 | Batz | 23/230 B |
| 4,282,001 | 8/1981 | Klose | 23/230 B |

*Primary Examiner*—Sidney Marantz
*Attorney, Agent, or Firm*—Bacon & Thomas

[57] ABSTRACT

A biochemical agent for facilitating detection of immunological agglutination reactions in liquid suspensions, in particular red blood cell suspensions. The biochemical agent includes from about 0.1 to about 1 g/l of a protein-compatible, water-soluble, non-ionic surface-active polyoxyalkylene ether or ester and from about 0.1 to about 1.0 g/l of a protein compatible water-soluble anionic detergent dissolved in a buffered isotonic aqueous saline solution. When added to an agglutination reaction mixture, this biochemical agent increases the sensitivity of the agglutination reaction and promotes fast settling out of agglutinated matter from the reaction mixture, whilst non-agglutinated matter is maintained in suspension and can easily be detected therein visually by the naked eye or nephlometrically. Also, a device for automated detection of agglutination reactions in liquid suspensions. The device comprises a loading unit for receiving conventional test tube carriers carrying test tubes with the liquid suspension transport means for carrying the test tube carrier from the loading unit to two dispensing units for dispensing reagents into the test tubes, a reacting unit wherein reaction is allowed to complete, a reading unit wherein nonagglutinated suspended matter in the test tubes is detected by means of a nephlometer and finally to an unloading unit. The biochemical agent and the device for detecting immunological agglutination are particularly useful in methods for blood grouping.

7 Claims, 1 Drawing Figure

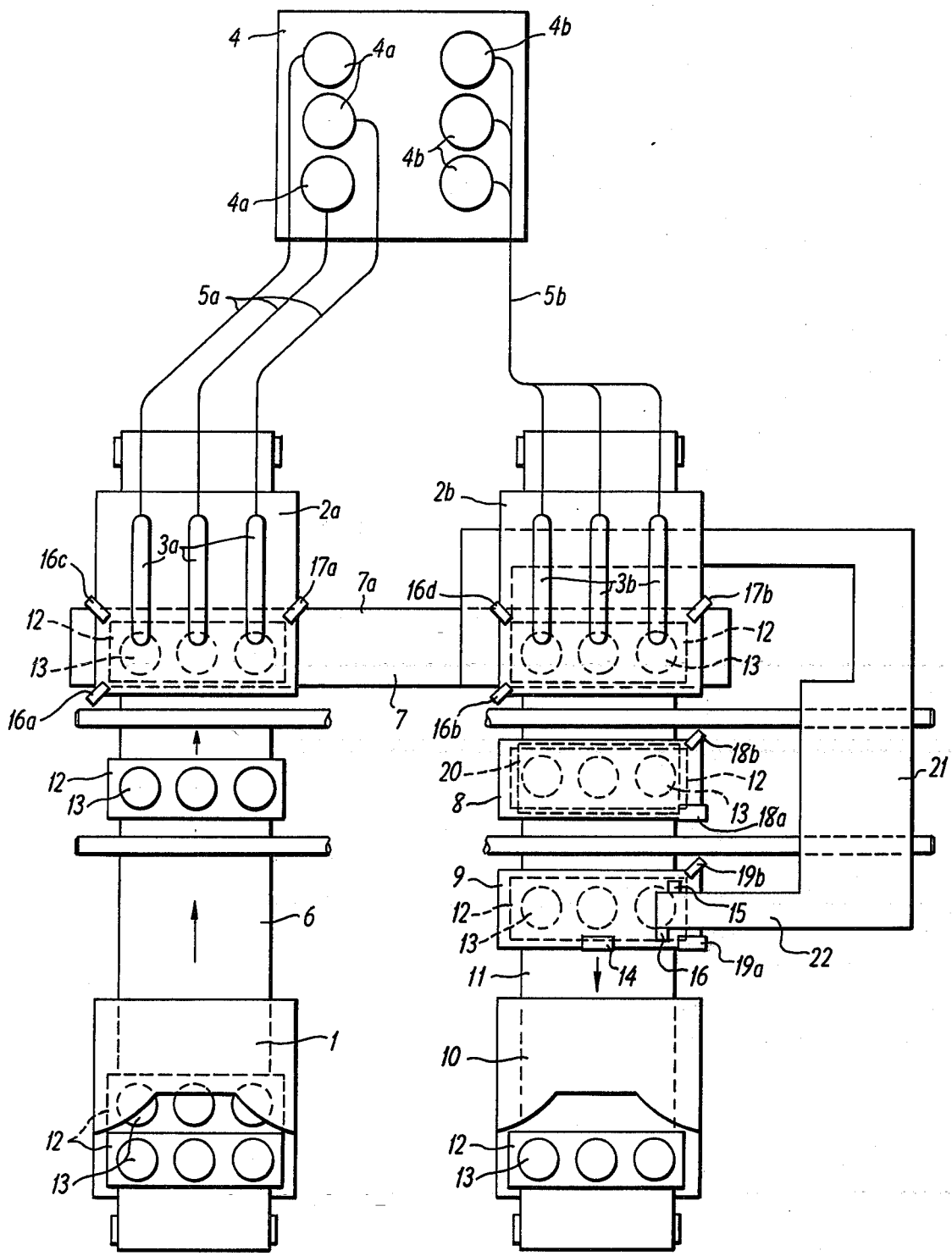

METHOD FOR DETECTING IMMUNOLOGICAL AGGLUTINATION AND BIOCHEMICAL AGENT THEREFOR

BACKGROUND OF THE INVENTION

The present invention pertains to a biochemical agent and its use in immunological analysis as an adjuvant in a method for visualizing immunological agglutination reactions in liquid suspensions and for detecting therein aggultinable components which are agglutinable with a given agglutinating agent, and an apparatus for automating said method. In particular, the present invention pertains to a biochemical agent and a method for blood grouping, and an apparatus for automating blood grouping.

It is well known in the medical art that the bloods of different persons usually have different antigenic and immune properties and that four major blood groups exist which are distinguished from each other by the presence or absence of two different but related antigens, that is antigen A and antigen B in the red cells, blood of the group A containing only antigen A, blood of group B containing only antigen B, blood of group O containing neither antigen A or B and blood of group AB containing both antigen A and B. The presence in the cells of the antigens which are capable of an immunological reaction with their respective bodies makes the cells susceptible to agglutination; these antigens therefore are called agglutinogens. When an antigen is not present in a person's red blood cells, the respective antibodies, called agglutinins, develop in its plasma. Thus blood of the group A contains anti-B antibodies in its serum and group O blood contains both anti-A and anti-B agglutinins. When bloods are mismatched so that anti-A or anti-B antibodies are mixed with red blood cells containing A or B antigens respectively the red cells agglutinate due to the immunological antigen/antibody reaction. This causes the cells to clump and plug up blood vessels. In addition to the O-A-B blood system, there are several other systems for distinguishing different bloods, which are sometimes important in the transfusion of blood, e.g., the Rh system. Different bloods are distinguished by the presence of different Rh-agglutinogens called Rh-factors.

Accordingly, in order to avoid blood mismatching in blood transfusion, it is necessary to determine the blood group of the recipient and of the donor blood. Blood grouping therefore is routinely done in medical laboratories and in blood banks, and there is a need for fast and simple blood grouping methods.

Principally blood grouping is done by contacting a small amount of a suspension of the red blood cells with known antisera, e.g., anti-serum A (containing agglutinin A) and anti-serum B (containing agglutinin B) and observing whether or not agglutination occurs. Generally blood grouping and related immunological tests are done by manual procedures. The usual method of blood typing is the slide technique. Earlier the blood was diluted with saline to obtain a suspension of red blood cells and a drop of the saline suspension was mixed with a drop of the antiserum directly on a slide, and after allowing several minutes for the agglutination to take place, the slide was observed either by the naked eye or under a microscope to determine whether or not cells had clumped. According to a more reliable now commonly used method the red cell suspension and the antiserum are mixed in a small test tube and the mixture is centrifuged in a special centrifuge for 30 to 60 seconds. Whether or not agglutination has taken place is then examined by the naked eye while gently agitating the deposit in the tube or by transferring the deposit onto a slide and examining it microscopically.

More recently devices for automating the blood grouping procedure have been proposed. U.S. Pat. Nos. 3,334,018 and 3,624,223 pertain to blood grouping assemblies wherein blood samples and antisera as well as air are pumped into a device wherein a segmented stream of segments of liquid mixture interrupted by segments of air is formed and passed through a series of helical mixing coils. During the passage through a series of separating devices the relative denser agglutinated cells are removed from the samples. According to U.S. Pat. No. 3,334,018 the samples are subsequently hemolyzed and the stream is colorimetrically analyzed with respect to its hemoglobin content. According to U.S. Pat. No. 3,624,223 the samples are subsequently analyzed for color intensity by a filter paper method.

U.S. Pat. No. 3,432,268 discloses an apparatus for automated blood grouping wherein a stream of a suspension of blood cells is continuously mixed with continuously changing amounts of the antisera in a reaction coil and the fluctuation in the light transmission of the resulting reaction stream is continuously measured in a flow cuvette.

Another device for partially automated blood grouping comprises a plurality of centrifugation discs having especially shaped test cuvettes inserted therein. The reaction between a blood cell suspension and the antisera takes place in the test cuvettes, and after centrifugation it is determined whether cell agglutinations have formed.

The hitherto known devices for automated blood grouping methods each comprise an assembly of a large number of highly specialized equipments and accordingly are costly to produce and space consuming.

SUMMARY OF THE INVENTION

It is an object of the present invention to provide a biochemical agent which facilitates the recognition of immunological agglutination reactions in liquid suspensions in immunological test methods, in particular blood grouping methods which may be carried out in a substantially manually or in at least partially automated procedure.

it is an especial object of the present invention to provide a biochemical agent and test method which increases the sensitivity of the agglutinable matter in the test sample, e.g., the red blood cells, containing the antigens or agglutinogens and of the agglutination-causing reagent, e.g. the antisera, containing agglutinins or antibodies thus allowing to reduce the amount of reactants used per test and eliminating the risk that a weak positive reaction is not detected and the need to use enzyme preparations presently used for weak reactions.

It is a further especial object of the present invention to provide a biochemical agent which accelerates agglutination reactions and promotes fast and substantially complete settling out of agglutinated matter, e.g., cell agglutinations, from a liquid suspension while maintaining substantially all non-agglutinated matter, e.g., non-agglutinated cells, in suspension for a long period of time e.g., up to several hours, and increasing the area of visualization.

In particular, it is an object to provide a biochemical agent and an improved method for detecting agglutination of red blood cells in a liquid suspension, especially a method for blood grouping which eliminates the need for washing the red blood cells and/or preparing diluted suspensions thereof prior to carrying out the determination, eliminates the need for centrifugation of the test reaction mixture and eliminates the need for microscopic examinations. It is a further object of the present invention to provide such a biochemical agent and method which can be carried out in conventional test tubes, allows fast and simple detection of cell agglutination by visual or nephlometric inspection of the test liquid for the presence or absence of suspended cells therein, and which provides within the test liquid a sufficiently complete separation between settled out agglutinated cells and suspended unagglutinated cells to eliminate the risk of not detecting evan a weak positive reaction or of misinterpreting a negative reaction.

It is a further object of the present invention to provide an apparatus for automated detection of agglutinable components in a liquid suspension, in particular an apparatus for automated blood group determination, wherein the drawbacks of the prior art devices are avoided, and wherein the determination can be carried out in conventional test tubes in a simple manner using a biochemical agent which facilitates recognition of immunological agglutination eliminating the need for washing or diluting steps prior to the determination, and the need for centrifugation.

It is a further especial object of the present invention to provide such an apparatus the various components of which can be produced at relatively low cost and which can take the form of a a space saving table top model which requires only such a small space that it can be easily installed on a conventional table.

In order to accomplish the foregoing objects there is provided a biochemical agent for improving the detectability of immunological agglutination reactions in liquid suspensions which comprises a solution of from about 0.1 to about 1.0 g/l of nonionic surface-active agent selected from the group consisting of water-soluble protein-compatable polyoxyalkylene ethers and esters and from about 0.1 to about 1 g/l of a watersoluble protein-compatable anionic detergent, in an aqueous isotonic buffered solution having a pH value of from about 6.5 to about 8.0 and exhibits an osmolarity of from about 300 to about 400 milliosmol/kg, a sodium content of from about 125 to about 225 milliequivalents and a potassium content of from about 3.5 to about 7.5 milliequivalents per liter.

This biochemical agent is particularly useful as adjuvant in blood group determinations.

Furthermore, there is provided according to the present invention a method for detecting immunological agglutination in a liquid suspension, which comprises the steps of
 (a) mixing a liquid suspension susceptible of comprising agglutinogen-containing agglutinable matter suspended therein with a reagent susceptible of containing agglutinins reactive towards the agglutinogen-content of the agglutinable matter to obtain a reaction mixture
 (b) allowing a period of time suitable for an immunological reaction to take place
 (c) mixing the reaction mixture with the biochemical agent as defined above to obtain a diluted reaction mixture, and
 (d) examining the diluted reaction mixture for unagglutinated subject matter suspended therein.

In particular the foregoing method provides an improvement in blood grouping procedures. An improved blood grouping method according to the present invention comprises mixing a sample of the blood with the antiserum, allowing a suitable period of time, e.g., between about 1 and about 10 minutes, for an immunological reaction to take place in the reaction mixture and subsequently mixing the reaction mixture with an amount of preferably between about 10 and about 20 times its volume of the biochemical agent, to obtain a diluted reaction mixture. In the resulting diluted reaction mixture agglutinated cells are substantially settled out and non-agglutinated cells are substantially kept in suspension. Accordingly, a simple visual inspection of the diluted reaction mixture or a nephlometric detection of suspended subject matter therein are sufficient for a reliable determination of whether or not the red cells of the blood sample are agglutinated by the given antiserum, and thus to determine the blood group.

Furthermore, there is provided according to the present invention an apparatus for automated detection of agglutinable matter suspended in a liquid suspension, comprising
 (a) a loading unit for receiving a carrier for a plurality of test tubes containing the liquid suspension
 (b) a first dispensing unit comprising a plurality of first dispensing means for simultaneously dispensing a metered amount of iquid into each of the test tubes in the carrier,
 (c) a second dispensing unit comprising a plurality of second dispensing means for simultaneously dispensing a metered amount of liquid into each of the test tubes,
 (d) a storage unit comprising a plurality of first storage containers for a plurality of first liquid reagents each connected by means of a connecting tube to one of the dispensing means of one of the dispensing units, and a second storage container for a second liquid reagent connected by means of a connecting tube to the dispensing means of the other of the dispensing units,
 (e) a first transport means connecting the loading unit with the first dispensing unit for transporting said carrier from the receiving unit to the first dispensing unit,
 (f) a second transport means for transporting the test tube carrier from the first dispensing unit to the second dispensing unit,
 (g) a reacting unit comprising an oscillating means,
 (h) a reading unit comprising a photometric system comprising a light source for passing beams of light into the test tubes and light sensitive means for sensing the light emitted from the test tubes,
 (i) an unloading unit for discharging the carrier, and
 (j) a third transport means for transporting the carrier from the second dispensing unit through the reacting unit and the reading unit to the unloading unit.

According to a preferred embodiment of the invention, the apparatus is adapted for detecting immunological agglutination reactions, e.g., in liquid cell suspensions, in particular for blood grouping. For this purpose, the first dispensing means are connected each to one of the plurality of first storage containers each containing a reagent susceptible of containing agglutinins reactive towards the agglutinogen-content of the agglutinable matter suspended in the liquid suspension, and the second dispensing means are connected to the second storage container containing an agglutination detecting adjuvant, e.g., the biochemical agent of the present invention. For blood grouping the reagents contained in the first storage containers are antisera.

Further objects, features and advantages of the present invention will become apparent from the following detailed description of the invention and its preferred embodiments when considered in connection with the accompanying figure of drawings.

BRIEF DESCRIPTION OF THE DRAWINGS

FIG. 1 represents a schematic view of an embodiment of the apparatus according to the present invention.

DETAILED DESCRIPTION OF THE INVENTION

It has been found that the sensitivity of immunological agglutination reactions can be improved and the distinction between agglutinated matter and non-agglutinated suspended matter can be largely facilitated by adding to the reaction mixture of the liquid suspension to be examined for agglutinable matter suspended therein and the reagent susceptible of causing an agglutination reaction a biochemical agent which is a solution of a water soluble protein-compatable nonionic surface-active agent and a water soluble protein-compatable anionic detergent in an aqueous isotonic solution as defined above.

The isotonic aqueous buffered solution suitably is an isotonic saline solution comprising sodium chloride, potassium chloride and an alkali phosphate buffer which is buffered to a pH of from about 6.5 to about 8.0 preferably of from about 7.2 to about 7.4.

The sodium content of the biochemical agent is between about 125 and about 225, preferably between about 150 and about 200, most preferably about 175, e.g., 175±10, milliequivalents of sodium per liter.

The potassium content of the biochemical agent is between about 3.5 and about 2.5, preferably between about 4.3 and about 6.3 milliequivalents of potassium per liter.

The osmolarity of the biochemical agent is from about 300 to about 400 preferably from about 330 to about 350 milliosmol/kg.

A high degree of clearness and substantial absence of any suspended particles are required in the biochemical agent, e.g., the nephlometric background count should be less than 100 particles/ml.

Both the nonionic surface-active agent and the anionic detergent must be highly water soluble and must be compatable with proteins. In particular, they must be free of complex-forming or precipitating effects toward the proteinous matter in the agglutination reaction mixture.

The nonionic surface-active agents within the biochemical agent of the present invention include polyoxyalkylene ethers and esters.

The polyoxyalkylene moiety of the compounds may contain recurring oxyethylene alone or in admixture with oxypropylene units and preferably is a polyoxyethylene residue of sufficient length to provide water solubility to the compounds, e.g., a polyoxyethylene residue containing from about 6 to about 25, preferably from about 10 to about 25 oxyethylene units.

Suitable polyoxyalkylene ethers include ethers of the polyoxyalkylene with straight or branched alkyl or alkenyl alcohols containing between about 6 and about 25 preferably between about 9 and about 20 carbon atoms, such as nonyl alcohol trimethylnonyl alcohol, lauryl alcohol, stearyl alcohol, palmityl alcohol, oleyl alcohol or cetyl alcohol, or with phenyl alkyl alcohols containing up to 25 carbon atoms such as nonylphenyl alcohol; and ethers of the polyoxyalkylene with sorbitan fatty acid esters, e.g., sorbitan mono- and diesters of saturated and unsaturated fatty acids containing from about 12 to about 20 carbon atoms, such as sorbitanmonolaurate, sorbitanmonopalmate, soributan monostearate, sorbitan monooleate, sorbitan dioleate.

Suitable polyoxyalkylene esters include esters of the polyoxyalkylene with fatty acids containing from about 12 to about 20 carbon atoms such as lauric acid palmitic acid, stearic acid or oleic acid.

Suitable polyoxyethylene ether and esters can be represented by the following formula I $$H(CH_2-CH_2O)_nR$$ 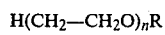

wherein n represents a number of from about 6 to about 25 and R represents alkyl or alkenyl containing from about 6 to about 25 carbon atoms, phenylalkyl containing from 7 to about 25 carbon atoms, alkylcarbonyl or alkenylcarbenyl containing from about 12 to about 20 carbon atoms, or a sorbitan mono or diester of an alkylcarboxylic or alkenylcarboxylic acid containing from about 12 to about 20 carbon atoms.

Among the foregoing, polyoxyethylene ethers and esters, compounds wherein R is alkyl containing 12 to 16 carbon atoms and n is a number from about 20 to about 25, in particular polyoxyethylene-23-laurylether, are preferred.

Any conventional anionic detergent which is sufficiently water soluble and protein-compatable can be used within biochemical agent.

Suitable anionic detergents include alkali, e.g., sodium or potassium, ammonium, lower alkyl amine, e.g., triethylamine and lower hydroxyalkylamine, e.g., triethanolamine, salts, preferably sodium salts, of organic derivatives of sulphur-oxygen acids such as alkyl-, alkylether- and alkylphenyl sulfates and sulfonates, and organic derivatives of phosphor-oxygen acids such as alkyl-, alkylether- or alkylphenyl phosphates and phosphonates.

Particularly suitable organic sulfates include alkylsulfates of the formula II and alkylether sulfates of the formula III $$R-OSO_3^-$$  II 

$$RO(CH_2-CH_2O)_xSO_3^-$$  III 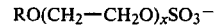

wherein R is alkyl containing from about 6 to about 20 carbon atoms, in particular from about 12 to about 18 carbon atoms, and x represents a number of from 1 to about 9 preferably from about 3 to about 5. Examples of suitable alkyl groups R include lauryl, myristyl, stearyl, 2-ethylhexyl or cetyl. Laurylsulfate and laurylether sulfates containing 3 to 5 oxyethylene units are preferred.

Suitable organic sulfonates include alkane sulfonates of the formula IV and alkylbenzene sulfonates of the formula V $$R-SO_3^- \quad \text{and}$$  IV 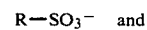

-continued

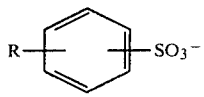

wherein R is as defined above.

Suitably the biochemical agent comprises from about 0.1 to about 1.0, preferably from about 0.5 to about 1.0 g/l of the nonionic surfactant and from about 0.1 to about 1, preferably from 0.5 to 1.0 g/l of the anionic detergent.

The present invention provides an important improvement in immunological test procedures for detecting agglutination reactions.

According to the method of the present invention for detecting immunological agglutination in a liquid suspension, a liquid suspension susceptible of containing agglutinable matter suspended therein and a reagent susceptible of containing agglutination-causing components are reacted with each other in a conventional manner, the resulting reaction mixture is mixed with the biochemical agent and the resulting diluted reaction mixture is examined for non-agglutinated matter retained in suspension therein.

Addition of the biochemical agent to the agglutination reaction mixture provides several important advantages:

(a) the sensitivity of the agglutinable matter and the agglutination-causing components in the reaction mixture is increased leading to a substantially complete agglutination, even in the case of an only weak activity per se of the agglutinating components of the reaction mixture;

(b) the speed of the agglutination reaction is accelerated;

(c) the need of a purifying and/or diluting pretreatment of the liquid suspension of the agglutinable matter is eliminated. It is believed that the foregoing advantages are largely due to the presence of the detergent in the biochemical agent, e.g., a washing effect of the detergent on the suspended particles of agglutinable matter;

(d) settling out of agglutinated matter is promoted whereas non-agglutinated matter is maintained substantially completely in suspension for a prolonged period of time, e.g., for a period of up to several hours. This advantageous stabilization of the suspension of suspended non-agglutinated matter is believed to be largely due to the effect of the nonionic surfactant in the biochemical agent;

(e) due to the substantially complete separation of settled out agglutinated matter from suspended nonagglutinated matter in the diluted reaction mixture containing the biochemical agent, determination of whether or not an agglutination has taken place can readily be made by visual inspection or by nephlometric inspection of the diluted reaction mixture, without the need of any separation-enhancing pretreatment, e.g., centrifugation of the mixture, and without need for microscopic inspection or use of highly sensitive photometric equipment.

The method according to the present invention is particularly useful in blood grouping procedures. Yet it is also applicable to any other immunological test methods involving an antigen/antibody agglutination reaction. Such immunological methods include, e.g., blood testing methods, such as Rh-typing of blood, crossmatching of blood, Coombe's test, and antibody screening, e.g., of drugs such as antibiotics, test of bacteria, virus or protein suspensions.

Accordingly, the term "agglutinogen-containing" and "agglutinable matter" containing liquid suspension are used herein to denote not only cell suspension, e.g., blood and blood cell suspensions but also suspensions of other proteineous or polymeric matter containing antigens or having agglutinogenic groups in their molecules, such as bacteria, latex or polymer suspensions.

The term "reagent" is used herein to denote not only antibody-containing liquids, such as antisera, but also test liquids which are susceptible of containing agglutinins or antibodies for a given agglutinable matter.

In a preferred embodiment, the method according to the present invention is used for blood grouping. The blood grouping procedure is carried out on a suspension of the red blood cells, which may be undiluted blood, an undiluted red cell containing fraction of the blood or a diluted red cell suspension having a red cell content of at least 2%, e.g., of from 2 to about 5%. Suitably an amount of from about 10 to about 150 microliters of the red cell suspension is used per test, preferably an amount corresponding to from about 10 to about 20 microliters of the undiluted red cell blood fraction. For example, if the test is carried out in a manual procedure it is advisable to use an amount of from 1 to about 5 drops, corresponding to from about 25 to 150 microliters of a diluted red cell suspension, whereas in an automated procedure preferably an amount of from about 10 to about 20 microliters of an undiluted red cell blood fraction is used. The blood grouping procedure comprises the steps of mixing a first sample of the red blood cell suspension with an effective amount of antiserum A, that is, an amount having a sufficient antibody content for agglutinating substantially the entire red cell content of the sample of red cell suspension in case these cells contain antigen A, e.g., an amount of from about 20 to 150 microliters, to obtain a first reaction mixture, mixing a second sample of the red blood cell suspension with an effective amount of antiserum B to obtain a second reaction mixture, allowing the reaction mixtures to stand for a period of time sufficient for an immunological antigen/antibody reaction to substantially take place in the reaction mixture, e.g., a period of between about 1 and about 10 minutes, mixing each of the reaction mixtures with the biochemical agent, e.g., with an amount of between about 10 and about 20 times its volume of the biochemical agent to obtain a first and a second diluted reaction mixture, allowing a period of time sufficient for completion of the immunological reaction and settling out of agglutinated cells, e.g., a period of from about 1 minute up to about 25 hours, preferably of between about 1 minute and about 5 minutes, and inspecting the diluted reaction mixtures visually or nephelometrically to determine whether nonagglutinated cells are retained suspended therein.

According to a further embodiment of the present invention there is provided an apparatus for automating the method for detecting immunological agglutination in a liquid suspension according to the present invention.

A schematic view of an embodiment of the apparatus is shown in FIG. 1.

The apparatus for automated detection of agglutinable matter in a liquid suspension is adapted for the use of conventional test tubes contained in a conventional test tube carrier which are commonly used in medicinal laboratories. Conventional test tubes of transparent material such as glass or transparent plastic material can be used. The test tubes can take any desired shape, e.g., the shape of round tubes or rectangular cuvettes. Each test tube carrier may carry a plurality of test tubes, e.g., up to about 12, in particular from 2 to about 10 test tubes, preferably arranged in a row.

The apparatus comprises a loading unit (1) for receiving a carrier (12) for test tubes (13), a first dispensing unit (2a) with first dispensing means (3a), a second dispensing unit (2b) with second dispensing means (3b), a storage unit (4) comprising first and second storage containers (4a and 4b) which each are connected to one of the dispensing units by means of connecting tubes (5a and 5b), a first transport means (6) connecting the loading unit (1) with the first dispensing unit (2a), a second transport means (7) connecting the two dispensing units (2a and 2b) with each other, a reacting unit (8) comprising ocillating means (20), a reading unit (9), an unloading unit (10) and a third transport means (11) connecting the second dispensing unit (2b) with the resetting unit (8), the reading unit (9) including a photometric system comprising a light source (14) and light sensitive means (15), and the unloading unit (10).

The loading unit (1) is adapted to receive one or several, e.g., a number of up to 6 test tubes carriers (12) at the same time.

The first transport means (6), which suitably is a conventional electrically driven transport belt, carries the test tube carrier to the first dispensing unit (2a).

Both, the first and the second dispensing units (2a, 2b) suitably are equipped with a means (16a, 16b) for detecting the presence of a test tube carrier (12), e.g., a mechanical switch which is tripped by the carrier and a means (16c and 16d), which is programmed to activate an electrical system for operating the dispensing means upon detection of the presence of a test tube carrier in the dispensing unit.

Furthermore, the first and second dispensing units each suitably are equipped with means (17a, 17b) for activating the subsequent transport means after completion of the dispensing operation. If desired, at least one of the activating means can be programmed such that the activation of the subsequent transport means is delayed for a given period of time after completion of the dispensing operation. If desired, the storage unit (4) may further comprise a means for sensing the amount of substance contained in each of the storage containers (4a and 4b) which means is further connected to an alarm system and is programmed to activate the alarm system, e.g., to flash a light, when the amount of substance in a storage container is below a given level.

The second transport means (7) which is activated after completion of the dispensing operation in the first dispensing unit carries the test tube carrier (13) in the direction of the arrow from the first dispensing unit (2a) to the second dispensing unit (2b).

The third transport means (11) which is activated after completion of the dispensing operation in the second dispensing unit then carries the test tube carrier (12) in the direction of the arrow through the reacting unit (8) and the reading unit (9) to the unloading unit (10).

The reacting unit (8) suitably is equipped with a stopper (18a) and a means (18b) for detecting the presence of the test tube carrier (12), e.g., a mechanical switch which is tripped by the test tube carrier (12), which is programmed to upon detection of the test tube carrier in the reacting unit (9) interrupt the operation of the third transport means (11) for a given period of time and to activate the oscillating means (20), e.g., an oscillating table, for a portion of said given period of time.

If desired, the dispensing units (2a, 2b) and/or the reacting unit (9) may further be equipped with a heating means for maintaining the test tubes at an elevated temperature, e.g., a temperature of about 37° C.

After completion of the given waiting period, the test tube carrier is carried on into the reading unit (9). Upon arrival of the test tube carrier (12) in the reading unit (9) operation of the third transport means (11) is again interrupted for a given period of time.

The individual components of the photometric system are of conventional design. The photometric system may be of the nephlometric type or the photo-spectrometric type. Preferably the photometric system is a nepholmeter of the light scatter detector system type. The portion of the test tube which is illuminated can be confined by means of movable or fixed screens.

If desired, the reading unit further comprises a sensing means (16) for sensing identification marks on the test tube carrier.

The reading unit (9) suitably is equipped with a stopper (19a) and means (19b) for detecting the presence of the test tube carrier (12), e.g., a mechanical switch which is tripped by the carrier, which is programmed to activate the photometric system and the carrier identification sensing means.

Suitably the light sensitive means (15) and the carrier identification sensing means (16) of the reading unit are connected to a recording device, e.g., a pen recorder and/or to a computer programmed to identify the agglutinable components in the liquid suspension based on information transferred from the reading unit (9) and to record the results in form of a typed computer outprint.

According to a preferred embodiment of the apparatus according to the present invention, the first transport means (6) connecting the loading unit (1) with the first dispensing unit (2a) and the third transport means (11) connecting the second dispensing unit (26) with the unloading unit (10) are conveyor belts which are positioned parallel to each other and are movable in opposite direction, and the second transport means (7) connecting the two dispensing units (2a and 2b) is a shuttle means positioned transversally to the first and third transport means and includes a shuttle means (21) movable back and forth between the two dispensing units over a surface (7a). On the first and the third transport means the test tube carriers are carried in opposite directions transversally to their length. On the second transport means one test tube carrier at a time is transported in the direction of its length from the first dispensing unit to the second dispensing unit by the shuttle (21).

Preferably the means (18) for detecting a test tube carrier in the reacting unit (8) and interrupting the operation of the third transport means (11) is interrelated with the activating means (19), (17a) and (17b) and the distance between the units of the apparatus and the speeds of the transport means are adjusted such that a test tube carrier arrives at the reacting unit (8) at the same time at which the preceding test tube carrier arrives at the reading unit (9) and both carriers remain in these respective units for the same given period of time for which the operation of the third transport means (11) is interrupted, and that during this period of time the second transport means (7), that is the shuttle means, carries a subsequent test tube carrier from the first dispensing unit (2a) to the second dispensing unit (2b) and travels back to the first dispensing unit (2a).

According to a preferred embodiment of the apparatus the light sensitive means (15) and the means (16) for sensing identification marks on the test tube carrier within the reading unit (9) are rigidly mounted onto the shuttle (21) by means of a support member (22). In this manner while the shuttle moves from the first dispensing unit (2a) to the second dispensing unit (2b) and back to the first dispensing unit (2a), the sensing means (16) and the light sensitive means (15) are moved back and forth in the reading unit (9) in the direction of the length of the test tube carrier (12). Suitably the sensing means (16) is activated while the shuttle moves in the one direction and the light sensitive means (15) is activated while the shuttle moves back in the reverse direction.

The following example is intended to further illustrate the present invention without limiting it.

EXAMPLE

A. Preparation of a biochemical agent for detecting immunological agglutination reactions:

700 ml of a solution of 1.42 g of sodium hydrogen phosphate ($Na_2HPO_4$) in 1 liter of 0.9% sodium chloride solution and 300 ml of a solution of 1.36 g of potassium dihydrogen phosphate ($KH_2PO_4$) in 1 liter of 0.9% sodium chloride solution are mixed and the pH of the resulting buffered saline solution is adjusted to 7.2 at 20° C.

0.5 g of Brij 35$^{R*}$ and 0.5 g of Laureth sulphate** are added to 1 liter of the buffered saline solution and the mixture is stirred for 10 to 15 minutes by means of a magnetic stirrer.

*polyoxyethylene-23-lauryl ether, manufacturer Atlas Chemical Industries. **sodium laurylether sulfate containing 3-5 oxyethylene units per molecule.

B. Manual blood group procedure:

3 Samples of 2 drops of a 2-4% red cell suspension in saline each are introduced into a test tube, suitably by means of an automatic dispenser. Into each test tube one drop of a different antiserum, that is, antiserum A, B, or AB, are added simultaneously. The reaction mixtures in the test tubes are allowed to stand for two minutes. Then 1.5 ml of the biochemical agent are added to each of the tubes and the diluted mixtures are allowed to stand for 5 minutes. Subsequently the test tubes are examined visually by the naked eye to determine whether non-agglutinated cells are retained in suspension therein.

Additionally, the test tubes may be examined in a conventional nephlometer (light scatter detector system) to determine whether or not they contain non-agglutinated cells suspended therein.

C. Automated blood grouping procedure 10 microliter samples of the undiluted red cell blood fraction of the bloods to be grouped are introduced into test tubes (13) in a test tube carrier (12). Up to 6 test tube carriers are introduced into the loading unit (1) of the apparatus shown in FIG. 1, and the apparatus is turned on. The transport belt (6) carries the test tube carriers to the first dispensing unit (2a). The first carrier enters the dispensing unit (2a) thereby tripping the switch (16a) which starts operation of the dispensing unit (2a). The tips of the first dispensing means (3a) which each are connected to a different storage container (4a) containing each a different antiserum, enter the test tubes, an amount of 5 drops of the respective antiserum is dispensed in each of the test tubes, and the tips of the dispensing means are again removed from the test tubes. After a waiting period of two minutes after completion of the dispensing operation, the shuttle means (21) is activated and transports the test tube carrier to the second dispensing unit (2b). After the first carrier has left the first dispensing unit, a subsequent carrier is entered and the dispensing operation is repeated. Upon entering the second dispensing unit (2b) the first carrier is tripping the switch (16b) which starts the dispensing operation of the second dispensing unit (2b). The tips of the dispensing means (3b) which are connected to a storage container (4b) containing the biochemical agent, enter the test tubes, an amount of 3 ml (±10%) of the biochemical agent is dispensed into each of the test tubes and the tips of the dispensing means are again removed from the test tubes. After completion of the dispensing operation, the transport belt (11) is activated and transports the first test tube carrier to the reacting unit (8) thereby tripping switch (18b) which interrupts the operation of transport belt (11) for a period of 2 minutes and activates an oscillating table (20) for a period of 15 seconds. After the 2 minute interruption, operation of the transport belt (11) is resumed and the first test tube carrier is transported into the reading unit (9) thereby tripping switch (19b) which activates the light sensing means (15) and the means (16) for sensing the identification marks on the test tube carrier. At the same time, where the first test tube carrier enters the reading unit (9), the second test tube carrier enters the reacting unit (8) and the operation of transport belt (11) is again interrupted for a 2 minute period. During this period, the shuttle transport means (7) onto which the light sensing means (15) and the identification mark sensing means (16) are mounted by means of the support member (21) moves back and forth once between the two dispensing units (2a and 2b) and thereby moves the sensing means (15) and (16) back and forth in the direction of the length of the test tube carrier in the reading unit (9). The information from the sensing means is fed into a computer which is programmed to identify the blood group of the test sample based on this information and to print out the result in a computer read out.

After the operation of the reading unit (9) is completed, the test tube carrier is transported to the unloading station (10) where it is removed from the apparatus.

What is claimed is:

1. A biochemical agent comprising a solution of
from about 0.1 to about 1.0 g/l of a nonionic surface-active agent selected from the group consisting of water soluble protein-compatable polyoxyalkylene ethers and esters and of
from about 0.1 to about 1 g/l of a water soluble protein-compatable anionic detergent in
an aqueous isotonic buffered solution having a pH value of from about 6.5 to about 8.0; and exhibiting an osmolarity of from about 300 to about 400 milliosmol/kg, a sodium-contact of from about 125 to about 225 milli-equivalents/1 and a potassium content of from about 3.5 to about 7.5 milli-equivalents/1.

2. The biochemical agent as defined in claim 1 wherein the nonionic surface active agent is polyoxyethylene ether of a $C_{12}$–$C_{16}$ alkyl alcohol containing from about 20 to about 25 oxyethylene units and the anionic detergent is a $C_{12}$–$C_{16}$ alkyl sulfate or a $C_{12}$–$C_{16}$ alkyl ether sulfate containing 3 to 5 oxyethylene units.

3. The biochemical agent of claim 2 which contains from about 0.5 to about 1.0 g/l of the nonionic surfactant and from about 0.5 to 1.0 g/l of the anionic detergent.

4. The biochemical agent of claim 2 or 3 wherein the nonionic surfactant is polyoxyethylene-23-laurylether and the anionic detergent is laurylsulfate or laurylethersulfate and containing 3 to 5 oxyethylene units.

5. The biochemical agent of claims 1, 2 or 3 which has a pH of from about 7.2 to about 7.4, a sodium content of from about 150 to about 200 milliequivalents of sodium per liter, a potassium content of between about 4.3 and about 6.3 milliequivalents of potassium per liter, and an osmolarity of from about 330 to about 350 milliosmols per kg.

6. A method for detecting immunological agglutination in a liquid suspension, which comprises the steps of
 (a) mixing a liquid suspension comprising agglutinogen-containing agglutinable matter suspended therein with a reagent containing agglutinins reactive towards the agglutinogen-content of the agglutinable matter to obtain a reaction mixture;
 (b) allowing a period of time suitable for an immunological reaction to take place;
 (c) mixing the reaction mixture with the biochemical agent as defined in claim 1 to obtain a diluted reaction-mixture; and
 (d) examining the diluted reaction mixture for unagglutinated subject matter suspended therein.

7. The method as defined in claim 6 for blood grouping wherein step (a) comprises mixing a red cell suspension, which is an undiluted or diluted red cell containing fraction of a blood sample with an effective amount of an antiserum.

* * * * *